United States Patent
Bhuniya et al.

(10) Patent No.: US 10,502,742 B2
(45) Date of Patent: Dec. 10, 2019

(54) FLOURESCENT EXOMARKER PROBES FOR HYDROGEN SULFIDE DETECTION

(71) Applicant: AMRITA VISHWA VIDYAPEETHAM, Coimbatore (IN)

(72) Inventors: Sankarprasad Bhuniya, Coimbatore (IN); Nandita Mishra, Kollam (IN); Nithya Velusamy, Coimbatore (IN); Anupama Binoy, Kollam (IN); Kondapa Naidu Bobba, Coimbatore (IN); Divya Nedungadi, Kollam (IN)

(73) Assignee: AMRITA VISHWA VIDYAPEETHAM, Coimbatore (IN)

( * ) Notice: Subject to any disclaimer, the term of this patent is extended or adjusted under 35 U.S.C. 154(b) by 41 days.

(21) Appl. No.: 15/956,474

(22) Filed: Apr. 18, 2018

(65) Prior Publication Data

US 2018/0306792 A1   Oct. 25, 2018

(30) Foreign Application Priority Data

Apr. 18, 2017 (IN) .............................. 201741013739

(51) Int. Cl.
| | | |
|---|---|---|
| G01N 33/84 | (2006.01) | |
| G01N 33/574 | (2006.01) | |
| G01N 33/58 | (2006.01) | |
| C07F 9/655 | (2006.01) | |

(52) U.S. Cl.
CPC .... *G01N 33/57411* (2013.01); *C07F 9/65522* (2013.01); *G01N 33/582* (2013.01)

(58) Field of Classification Search
None
See application file for complete search history.

(56) References Cited

FOREIGN PATENT DOCUMENTS

CN         106279278 A    1/2017

OTHER PUBLICATIONS

Bae et al. (J. Am. Chem.Soc. (2013) 135: 9915-9923 (Year: 2013).*
English translation of Lin (CN 10629278; published Aug. 9, 2016) downloaded from Espacnet on Aug. 2, 2019 (Year: 2016).*
Chen et al. (Analyst (2013) 138: 946-951 (Year: 2013).*
Wei et al. (Chemistry: An Asian journal (2014) 9: 3586-3592 (Year: 2014).*
Elsayed et al. (Sensors and Actuators B: Chemical (2015): 987-994 (Year: 2015).*
Amdt S., et al., "Assessment of H2S in Vivo using the Newly Developed Mitochondria-Targeted Mass Spectrometry Probe MitoA," Journal of Biological Chemistry, May 12, 2017, vol. 292(19), pp. 7761-7773.
Maryanoff B., et al., "Stereochemistry of the Wittig reaction. Effect of Nucleophilic Groups in the Phosphonium Ylide," Journal of the American Chemical Society, Jan. 1985, vol. 107(1), pp. 217-226.
Wu Z., et al., "Visualizing Hydrogen Sulfide in Mitochondria and Lysosome of Living Cells and in Tumors of Living Mice with Positively Charged Fluorescent Chemosensors," Analytical Chemistry, 2016, vol. 88(18), pp. 9213-9218.

* cited by examiner

*Primary Examiner* — Susan M Hanley
(74) *Attorney, Agent, or Firm* — Convergence Intellectual Property Law P.C.; Jonathan Garfinkel

(57) ABSTRACT

A fluorescence probe with mitochondrial targeting and two-photon property, its preparation method and application in detecting and tracking endogenous $H_2S$ in samples or living cells. The fluorescent probe is prepared by a four-step preparation method and demonstrates a UV-vis absorption increment $\lambda_{ab}$=395 nm and ~43 fold higher fluorescence intensity in the presence of $H_2S$. The probe further demonstrates stability, selectivity for $H_2S$ over competing agents and sensitivity as low as 20 nm. A method of detecting endogenous $H_2S$ rapidly in the absence of any external stimulators is provided. Samples are contacted with the probe and the changes in fluorescence are monitored to detect $H_2S$ levels. The disclosed probe is non-toxic and suitable as a biomarker and therapeutic molecule in cancer and other diseases.

26 Claims, 13 Drawing Sheets

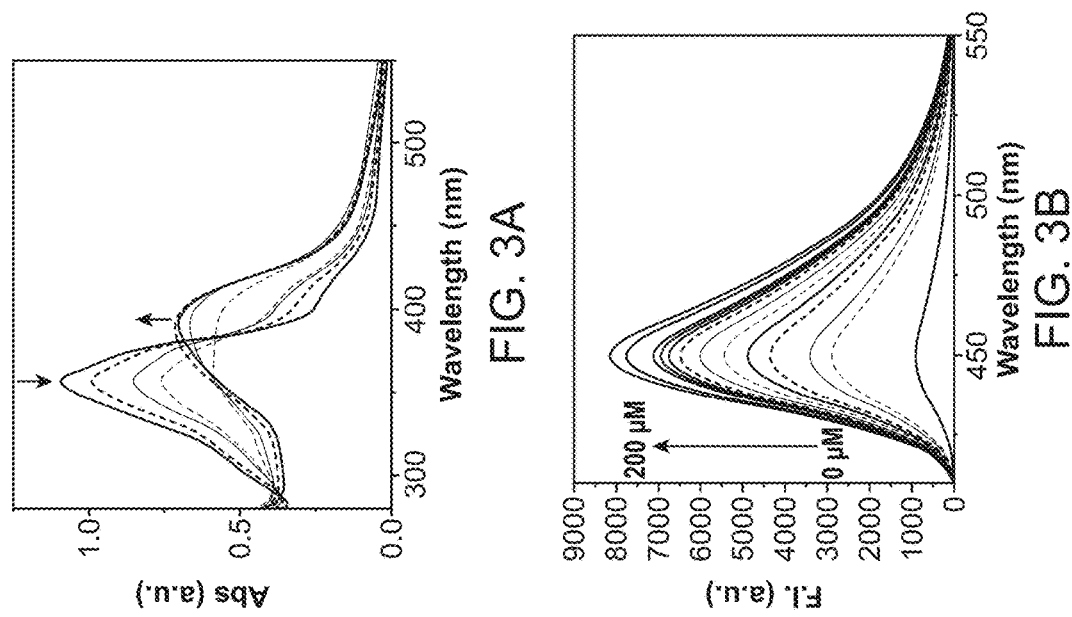
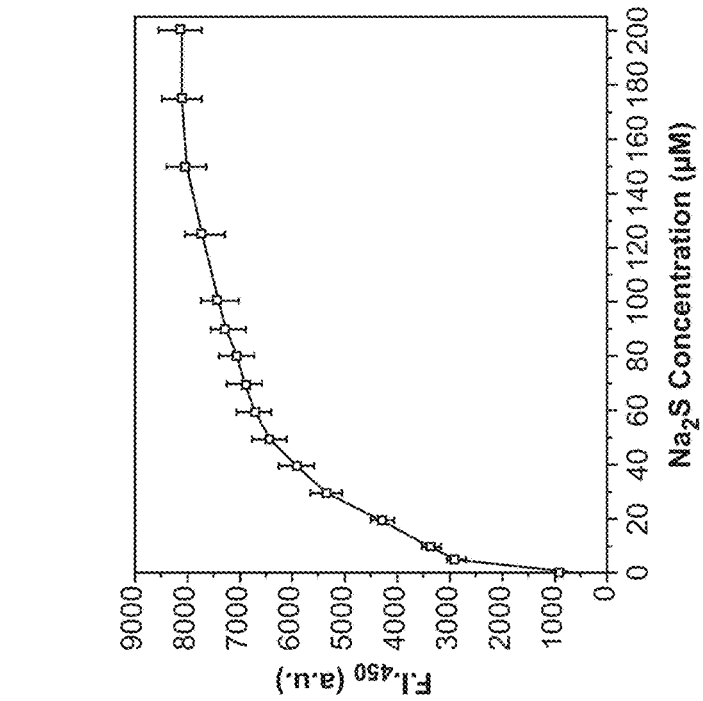
FIG. 3C
FIG. 3A
FIG. 3B

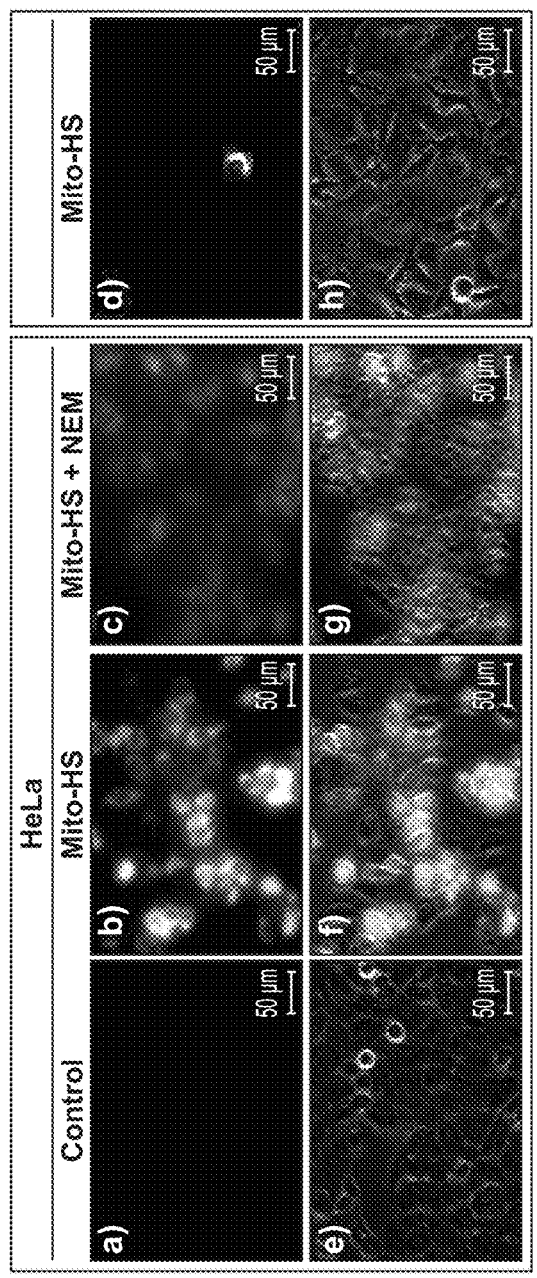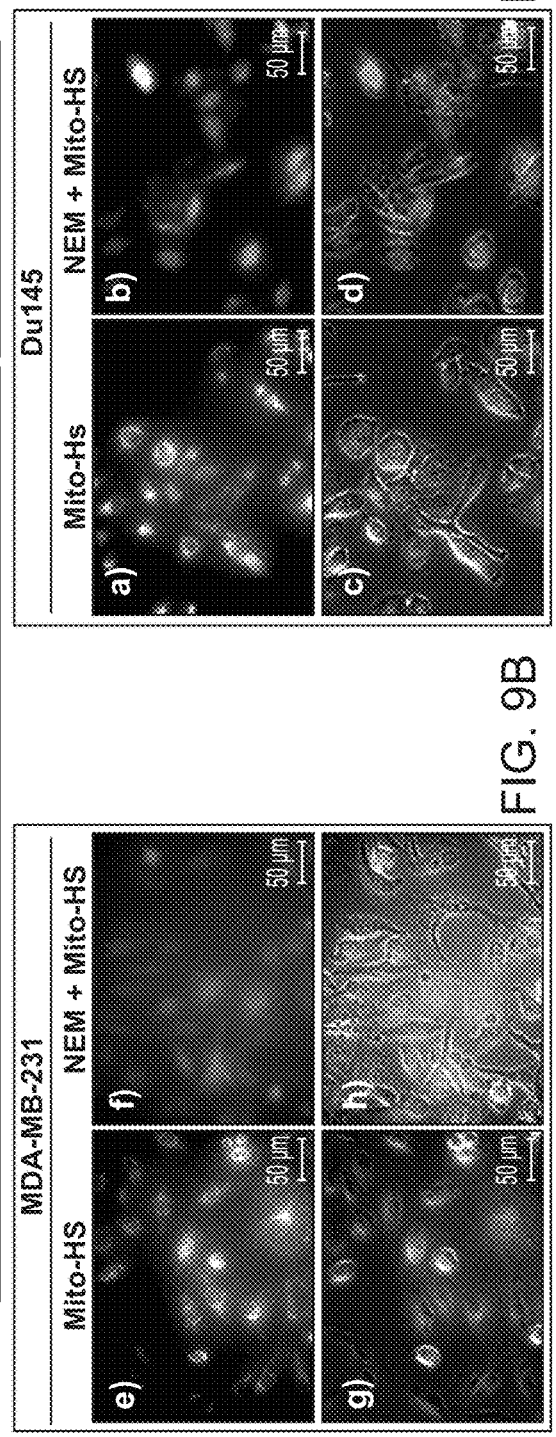
FIG. 9A
FIG. 9B
FIG. 9C

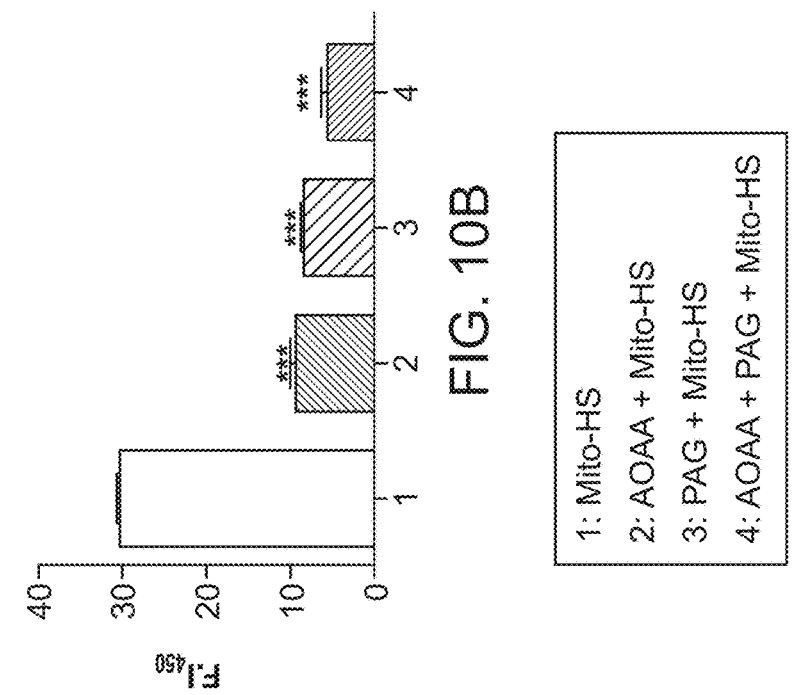
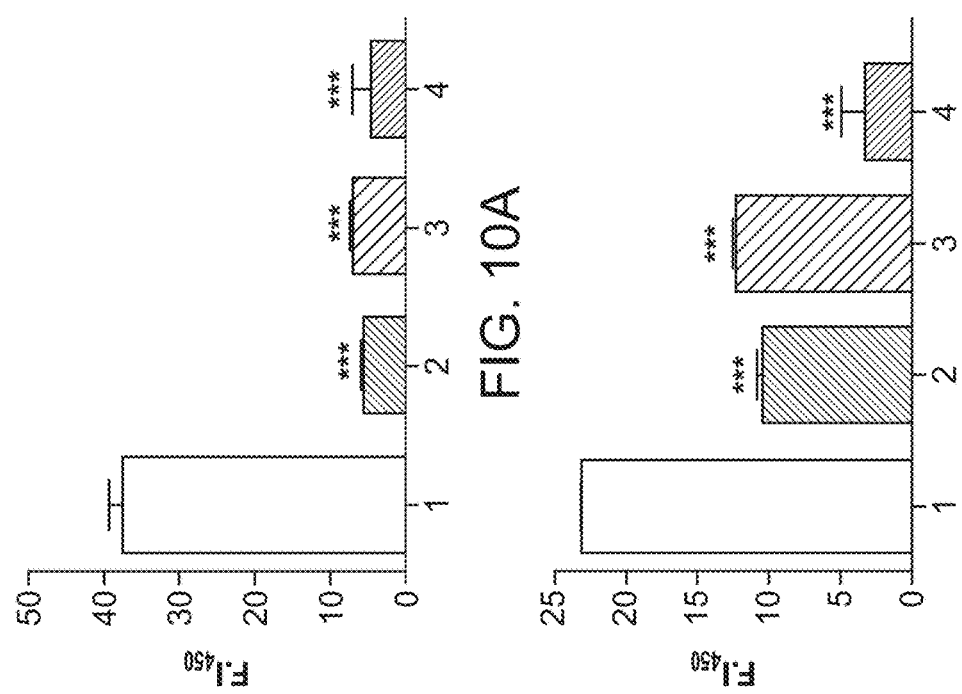
FIG. 10A, FIG. 10B, FIG. 10C
1: Mito-HS
2: AOAA + Mito-HS
3: PAG + Mito-HS
4: AOAA + PAG + Mito-HS

FLOURESCENT EXOMARKER PROBES FOR HYDROGEN SULFIDE DETECTION

CROSS-REFERENCES TO RELATED APPLICATIONS

This application claims priority to Indian patent application No. 201741013739, filed on 18 Apr. 2017, the full disclosure of which is incorporated herein by reference.

FIELD OF THE INVENTION

The present application is related to synthesis of fluorescent exomarker probes and in particular to a fluorescent exomarker probe for hydrogen sulfide detection.

DESCRIPTION OF THE RELATED ART

Hydrogen sulfide ($H_2S$) plays a key role in cellular signaling events such as a neurotransmitter in central nervous system of humans and mammals. $H_2S$ is generated in vivo enzymatically from sulfur containing amino acids such as cysteine and homocysteine in the presence of enzymes such as cystathionine-β-synthase (CBS), cystathionine-γ-lyase (CSE), and 3-mercaptopyruvate sulfurtransferase in a controlled manner in several organs such as heart, vasculature, brain, kidney, liver, lungs, pancreas, thoracic aorta, ileum, portal vein, and uterus. It can also be produced via non-enzymatic pathways and from the bacterial conversion of dietary substrates. Recent studies have revealed the imbalance in production of $H_2S$ is linked to several diseases including, Alzheimer's disease, Parkinson's disease and other neurodegenerative diseases along with possible risk for diabetes, arterial and pulmonary hypertension, dementia, diseases such as cirrhosis and gastric mucosal injury. Therefore, it remains an objective to measure and evaluate $H_2S$ levels in subjects.

Previous studies have described the diagnostic potential of $H_2S$ detection in pathological and non-pathological conditions such as hypoxia and cancer in different research works. Diagnostic methods based on colorimetric, electrochemical, mass spectrometry, and chromatographic assays to measure $H_2S$ have been described. However, these have been limited as diagnostic tools as they are unable to provide spatial and temporal information of in vivo concentration of $H_2S$ and its distribution in living cells and organisms. Currently, fluorescence imaging is a powerful technique for continuous observation of the dynamic intracellular processes of living cells. In recent years, fluorescent probes have been designed based on photo-induced electron transfer. Two-photon excitation (TPE) is a non-linear optical process, in which a fluorophore is excited via simultaneous absorption of two photons. Two-photon excited fluorescence has a characteristic dependence on the square of the square of excitation light intensity; doubling the excitation intensity, quadruples the fluorescence signal. So, TPE has added a new spectral dimension to fluorescence imaging.

$H_2S$ production is associated with dysfunctional mitochondrial activity associated with energy production, depolarization and cellular respiration. Moreover, CBS enzymes are reported to be localized to the outer layer of mitochondria in cancer cells. So it's important to detect mitochondrial $H_2S$ formation. It's a challenging task to detect $H_2S$ in a microenvironment like mitochondria over competing thiols due to difficulty of monitoring $H_2S$ and thiol levels simultaneously in complex environment of sulfur redox homeostasis. It remains a challenge so far detecting mitochondrial $H_2S$ specifically and accurately. Mitochondrial targeting $H_2S$ probe has attracted substantial interest as an emerging scope of research works.

Various publications have attempted to address this challenge. Publication number CN106279278A (Yifeng et al.) describes H2S detection by a mito-targeting fluorescent probe. Arndt et al., ("Assessment of H2S in vivo using the newly developed mitochondria-targeted mass spectrometry probe MitoA"), J. Biol. Chem. 2017, propose a mass-spectrometry based probe to detect H2S in mitochondria. Similarly, Wu et al., ("Visualizing Hydrogen Sulfide in Mitochondria and Lysosome of Living Cells and in Tumors of Living Mice with Positively Charged Fluorescent Chemosensors"), Anal. Chem., 2016, 88, 18, 9213-9218 demonstrate visualizing H2S in tumor cells with a mito-targeting probe. However, none of the prior arts reported a potent probing device to map endogenous H2S formation in cancer cells over normal cells. Furthermore, there remains a need for stable, non-toxic mitochondria-targeted probes which is readily taken up inside cells and can detect endogenous H2S accurately and specifically at sufficient resolution without supplementation with external stimulators thereby providing spatiotemporal information useful in diagnostic applications such as in cancer.

SUMMARY OF THE INVENTION

The present disclosure relates to hydrogen sulfide probe compounds, method of preparation thereof and application thereof as a diagnostic markers.

In one aspect, the present disclosure relates to a compound represented by formula (I) (Mito-HS)

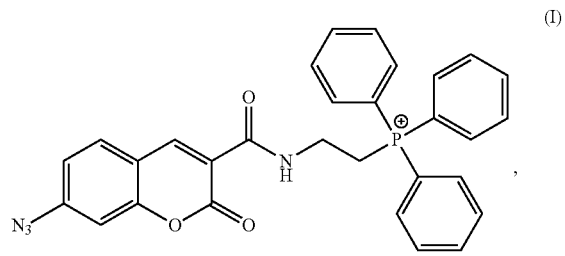 [SMILES: [N-]=[N+]=Nc1ccc2cc(C(=O)NCC[P+](c3ccccc3)(c3ccccc3)c3ccccc3)c(=O)oc2c1]

or a pharmaceutically acceptable salt thereof.

In another aspect, the present disclosure relates to a pharmaceutical composition including the compound of formula (I), or a pharmaceutically acceptable salt thereof, and a pharmaceutically acceptable carrier is provided.

In another aspect, the present disclosure relates to a composition for detecting a disease, guiding disease therapy, predicting disease relapse or prognosticating disease outcome in a subject, the composition including a suitable amount of the compound of formula I, or a pharmaceutically acceptable salt thereof. The disease may be a neurodegenerative disorder, diabetes mellitus, hypertension, dementia, cirrhosis, gastric mucosal injury, cardiovascular disease, hypoxia, or cancer. The neurodegenerative disorder may be Alzheimer's disease or Parkinson's disease. The cancer may be selected from cervical cancer, breast cancer, lung cancer, brain cancer, liver cancer, pancreatic cancer, colon cancer, leukemia, bone cancer, blood cancer, or ovarian cancer. The one or more agents may be selected from the group consisting of a monoclonal antibody, D-biotin, folic acid, or a combination thereof. The composition may be stable over a pH range of 4 to 9. The compound may be present in an amount in the range of 1-100 μM.

In another aspect, the present disclosure relates to a composition for detecting hydrogen sulfide in a sample including a population of cells, the composition including a suitable amount of the compound of formula I, or a pharmaceutically acceptable salt thereof. The population of cells may include cancer cells, cells from adipose, muscle, cartilage, bone, mucosa, lung, heart cells, brain, liver, kidney, pancreas, or vasculature, or a combination thereof. The composition may be at least 100 to 1000 fold selective for hydrogen sulfide over cysteine (Cys), $H_2O_2$, $NaNO_2$, $Cu(OAc)_2$, $Zn(OAc)_2$, $FeSO_4$, $FeCl_3$, $Na_2CO_3$, GSH, or ascorbic acid (AA). The suitable amount of the compound may be in the range of 10-600 μM. The composition may further include one or more agents selected from the group consisting of a monoclonal antibody, D-biotin, folic acid, or a combination thereof. The composition may be further configured to detect endogenous hydrogen sulfide levels in cells in the absence of external stimulators.

In another aspect, the present disclosure relates to a kit including the compound of formula I or a composition including the compound of formula I, or a pharmaceutically acceptable salt thereof; and instructions for use of the compound or composition.

In another aspect, the present disclosure relates to a method of detecting hydrogen sulfide in a sample, including the steps of: providing the sample comprising a population of cells; contacting the sample with a composition comprising a suitable amount of the compound of formula I, or a pharmaceutically acceptable salt thereof for a predetermined time period; and detecting a change in fluorescence for the sample using a fluorescence detector. The sample is excited in the range of 300-550 nm and the emission is detected in the range of 300-550 nm. The composition is configured to detect endogenous hydrogen sulfide levels in cells in the absence of external stimulators. Suitable amount is in the range of 10-600 μM. The sample may be pre-treated with a thiol-masking reagent. The thiol-masking reagent may be N-ethyl maleimide (NEM). The method may include visualizing the change in fluorescence using microscopy. The population of cells may include cancer cells, cells from adipose, muscle, cartilage, bone, mucosa, lung, heart cells, brain, liver, kidney, pancreas, or vasculature, or a combination thereof. The method may include determining the change in fluorescence of the sample is greater than that of a standard sample. The change in fluorescence is indicative of disease relapse or outcome. The composition may further include one or more agents selected from monoclonal antibody, D-biotin, folic acid, or a combination thereof.

In yet another aspect, the present disclosure relates to a process for preparing the compound of formula I. The process may include the steps: adding 4-bromo-2-hydroxybenzaldehyde to a first solution comprising diethylmalonate and piperidine to form a first compound represented by formula A;

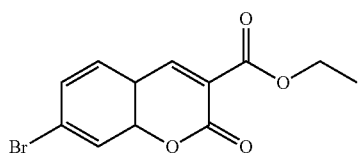

(A)

adding the first compound A in a second solution comprising sodium azide to form a second compound represented by formula B;

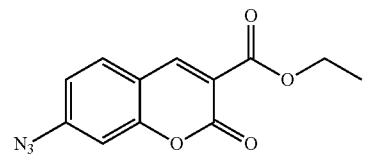

(B)

adding the second compound B to a third solution comprising NaOH to form a third compound represented by formula C; and

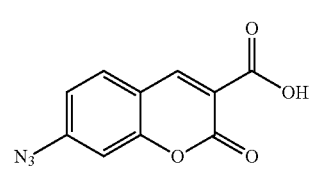

(C)

adding the third compound C to a fourth solution comprising a fourth compound represented by formula D,

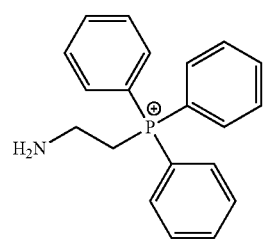

(D)

and a coupling agent to form the compound of formula I.

BRIEF DESCRIPTION OF THE DRAWINGS

Present embodiments have other advantages and features which will be more readily apparent from the following detailed description and the appended claims, when taken in conjunction with the accompanying drawings, in which:

FIG. 3A illustrates a UV-Vis absorption spectra of the probe (5 μM).

FIG. 3B illustrates a fluorescence spectra of the probe (5 μM).

FIG. 3C illustrates the fluorescence spectra of the probe (5 μM) recorded in the presence of variable concentrations of $Na_2S$ in PBS buffer (pH=7.4) containing 0.2% of DMSO.

FIG. 9A shows fluorescent microscopic images of untreated HeLa cells (a), HeLa cells treated with Mito-HS (5 µM) (b), cells pretreated with NEM prior to treatment with Mito-HS (5 µM) (c), along with the corresponding overlay of the fluorescence images with DIC Bright field images.

FIG. 9B shows fluorescent microscopic images of MDA-MB-231 cells treated with Mito-HS (5 µM) (e) and cells pretreated with NEM prior to treatment with Mito-HS (5 µM) (f) along with the corresponding overlay of the fluorescence images with DIC Bright field images (g and h).

FIG. 9C shows fluorescent microscopic images of DU-145 cells treated with Mito-HS (5 µM) (e) and cells pretreated with NEM prior to treatment with Mito-HS (5 µM) (f) along with the corresponding overlay of the fluorescence images with DIC Bright field images (g and h).

FIG. 10A shows cellular fluorescence quantification of HeLa cells.

FIG. 10B shows cellular fluorescence quantification of MDA MB 231 cells.

FIG. 10C shows cellular fluorescence quantification of DU145 cells.

DETAILED DESCRIPTION OF THE EMBODIMENTS

Figure 1A:
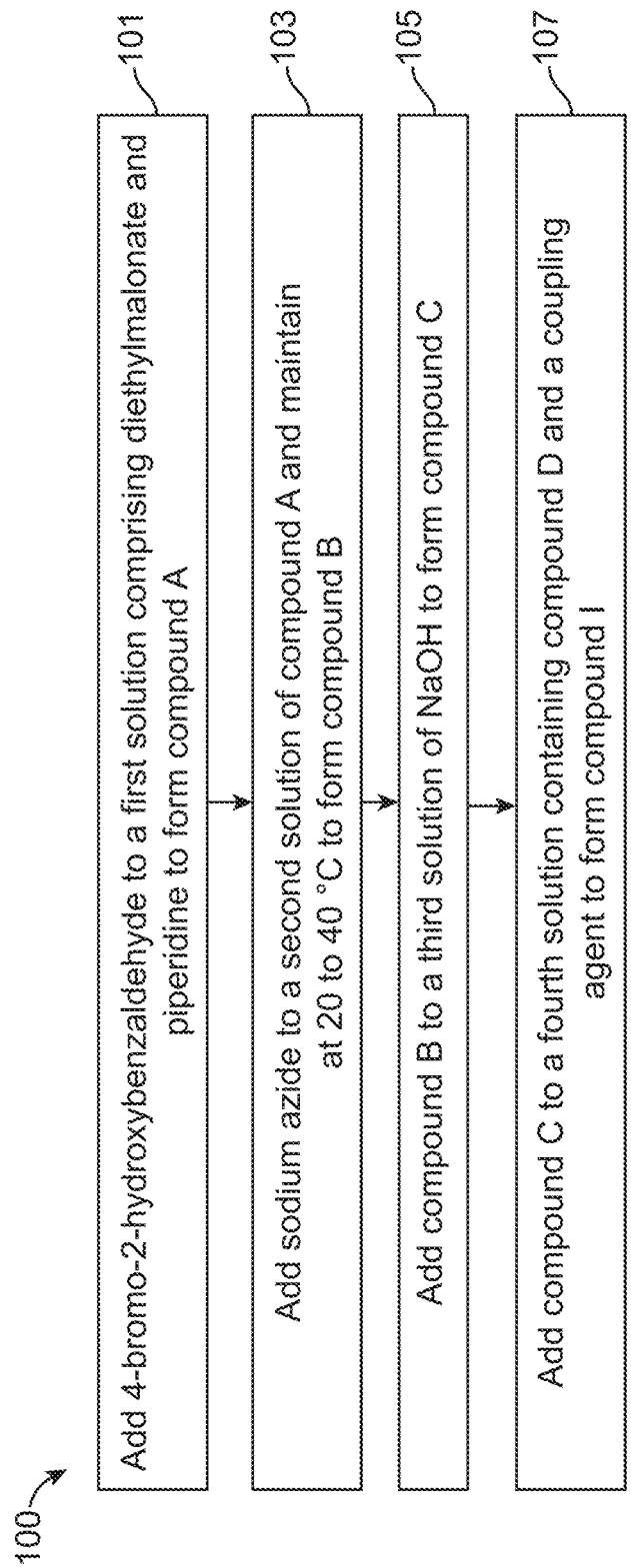
FIG. 1A depicts a method of preparation of hydrogen sulfide probe represented by formula I (Mito-HS).

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

Various embodiments relate to a compound of formula (I):

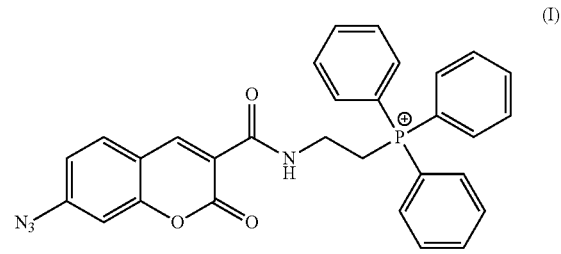

(I)

abbreviated as Mito-HS, or a salt thereof.

In one embodiment, the compound demonstrates a peak UV-vis absorption in the range of 300 to 450 nm. In another embodiment, the peak UV-vis absorption is about 370 nm. In some embodiments, the peak UV-vis absorption is about 395 nm in the presence of H$_2$S. In another embodiment, the compound demonstrates a peak fluorescence in the range of 400 to 550 nm. In some embodiments, the peak fluorescence is about 450 nm in the presence of H$_2$S. In some embodiments, the fluorescent derivative formed in the presence of H$_2$S is an aminocoumarin derivative. In some embodiments, the compounds are characterized by their $^1$H- and $^{13}$H-NMR chemical shifts. In one embodiment, compound I is characterized by $^1$H-NMR (400 MHz, DMSO-d$_6$): δ 8.95 (t, 1H, j=5.89 Hz), 8.78 (s, 1H), 7.98 (s, 1H), 7.86 (m, 9H), 7.75 (m, 6H), 7.29 (m, 1H), 7.22 (dd, 1H, j$_1$=4.89 Hz, j=12.01 Hz), 3.87 (m, 2H), 3.73 (m, 2H), 1.23 (s, 1H), and $^{13}$C-NMR (100 MHz, DMSO-d$_6$): 162.47, 155.65, 148.43, 145.92 131.95, 127.92, 119.11, 116.18, 115.89, 114.81, 106.32, 61.08, 13.99.

In some embodiments, a compound represented by formula (A), (B), or (C), or a pharmaceutically acceptable salt is provided.

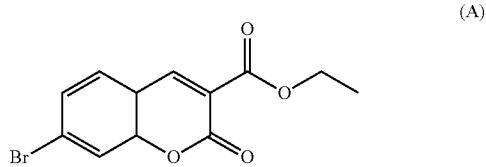 [SMILES: CCOC(=O)C1=CC2C=CC(Br)=CC2OC1=O]

(A)

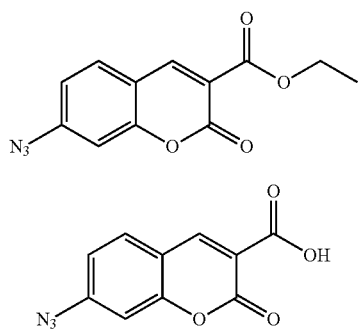

It will be understood that salts of the compounds of the various embodiments may be prepared, and such salts are included in the various embodiments including pharmaceutically acceptable salts. They may be any of the well-known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-aceloxybenzoic acids, or organic sulphonic acids, methane sulphonic, 2-hydroxyethane sulphonic, toluene-p-sulphonic or naphthalene-2-sulphonic acids. In addition to pharmaceutically-acceptable salts, other salts are included in the various embodiments. They may serve as intermediates in the purification of compounds or in the preparation of other, for example, pharmaceutically-acceptable salts, or are useful for identification, characterization or purification.

In some embodiments, a composition containing the compound I or a salt thereof is provided. The composition may additionally comprise a pharmaceutically acceptable carrier, vehicle, or excipient. A suitable amount of the composition may be used. In some embodiments, compound I is present in an amount in the range of 0.01-1000 μM in the composition. In some embodiments, the detection limit of the compound In some embodiments, the lower regression limit for detection is achieved at about 20-30 nm.

In some embodiments, the composition is at least 100 to 1000 fold selective for hydrogen sulfide over cysteine (Cys), $H_2O_2$, $NaNO_2$, $Cu(OAc)_2$, $Zn(OAc)_2$, $FeSO_4$, $FeCl_3$, $Na_2CO_3$, GSH, or ascorbic acid (AA). In other embodiments, the selectivity is higher than 1000 fold. In some embodiments, the composition is configured to detect endogenous hydrogen sulfide levels in cells selectively in the absence of external stimulators.

In some embodiments, the composition is stable over a pH range of 4 to 9. In other embodiments, the composition is stable in physiological conditions. In yet other conditions, the composition is stable in acidic conditions such as in tumor microenvironment.

In additional embodiments, the composition includes one or more agents. The agents may be a pharmaceutical agent, a diagnostic marker, a targeting molecule, a chemotherapeutic drug, a monoclonal antibody, a cofactor, a conjugate, a vitamin, D-biotin, folic acid, or a combination thereof. Such agents: may be formulated in any form such as dosage form, gel, capsule, liquid, sustained release, or the like; may be administered by any route such as parenteral, oral, topical, or the like; and using any technique known in the art such as by mixing, grinding, molding, or conjugation.

In some embodiments, the composition is used to detect a disease, guide disease therapy, predict disease relapse or prognosticate disease outcome in a subject. The disease may be a neurodegenerative disorder, diabetes mellitus, hypertension, dementia, cirrhosis, gastric mucosal injury, cardiovascular disease, hypoxia, or cancer. In some embodiments, neurodegenerative disorder is Alzheimer's disease (AD) or Parkinson's (PD) disease. Abnormal generation and metabolism of $H_2S$ have been reported in the pathogenesis of AD and PD. AD causes alterations in glutamate receptors; circuitry hyper-excitability; mitochondrial dysfunction; lysosomal failure and alterations in signaling pathways related to synaptic plasticity, neuronal cell and neurogenesis. Similarly, PD is a degenerative, progressive disorder that affects nerve cells in deep parts of the brain. In some embodiments, the composition is used to detect cancer. In some embodiments, cancer is selected from cervical cancer, breast cancer, lung cancer, brain cancer, liver cancer, pancreatic cancer, colon cancer, leukemia, bone cancer, blood cancer, or ovarian cancer. The increased production of $H_2S$ may be indicative of tumor growth and spread by stimulating cellular bioenergetics, activating proliferative, migratory, and invasive signaling pathways, and enhancing tumor angiogenesis. In some embodiments, the detected cells overexpress cystathionine-β-synthase (CBS) and/or cystathionine γ-lyase (CSE). In some embodiments, the compound is localized to the mitochondria of the cell. In other embodiments, the compound is used for tracking mitochondrial H2S formation in cells. In some embodiments, the composition does not detect normal cells.

In some embodiments, the composition is used for detecting hydrogen sulfide in a sample, which includes a population of cells. The cells may include human cells, animal cells, plant cells, cancer cells, cells from adipose, muscle, cartilage, bone, mucosa, lung, heart cells, brain, liver, kidney, pancreas, or vasculature.

As described above, the compositions of the present embodiments may additionally comprise a pharmaceutically acceptable carrier, adjuvant, excipient, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Except insofar as any conventional carrier medium is incompatible with the compounds of the embodiments, such as by producing any undesirable biological effect or otherwise interacting in a deleterious manner with any other component(s) of the pharmaceutically acceptable composition, its use is contemplated to be within the scope of various embodiments.

In yet other embodiments, a kit including any composition as described herein and instructions for use thereof is provided. The kit may include one or additional reagents such as a sample preparation reagent, detection reagent, or the like. The instructions for use describe a method for detecting hydrogen sulfide in a subject or cell sample using the kit.

Figure 1B:
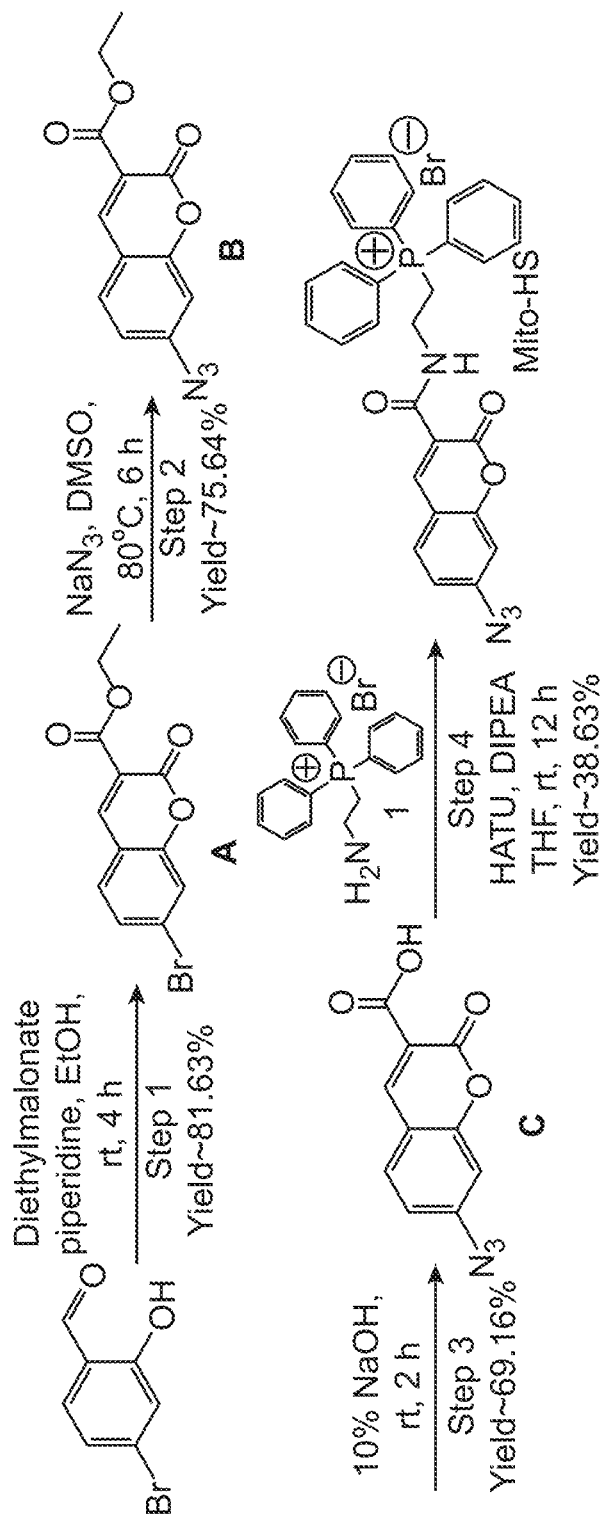
FIG. 1B depicts a reaction scheme for preparation of hydrogen sulfide probe represented by formula I.

In some embodiments, a method 100 of preparing Mito-HS is as illustrated in FIG. 1A. In step 101, to a solution of 4-bromo-2-hydroxybenzaldehyde in a suitable solvent, diethylmalonate and piperidine were added to obtain compound A. In step 103, to a solution of compound A in a suitable solvent, sodium azide was added and maintained at 20-40° C. for a predetermined period of time to obtain compound B. In step 105, compound B was dissolved in NaOH solution and allowed to react to obtain compound C. In step 107, to a solution of compound C, compound D was added with one or more additional reagents such as a coupling agent, HATU (1-[Bis(dimethylamino)methylene]-1H-1,2,3-triazolo[4,5-b]pyridinium 3-oxid hexafluorophosphate), or DIPEA (N,N-Diisopropylethylamine) in a suitable solvent to obtain the compound of formula I. In other embodiments, a method of preparing Mito-HS is as depicted in FIG. 1B.

Figure 2A:
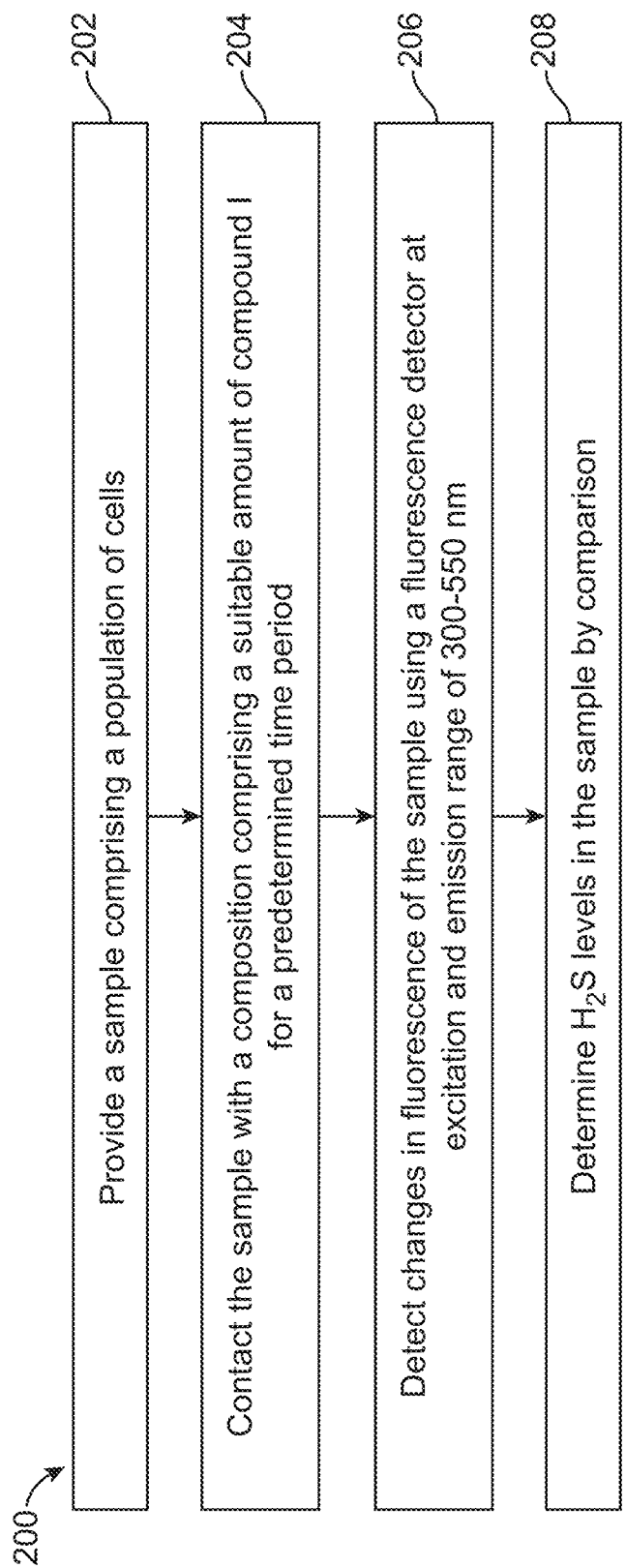
FIG. 2A shows a method of detecting endogenous hydrogen sulfide in a sample (A) using Mito-HS.
Figure 2B:
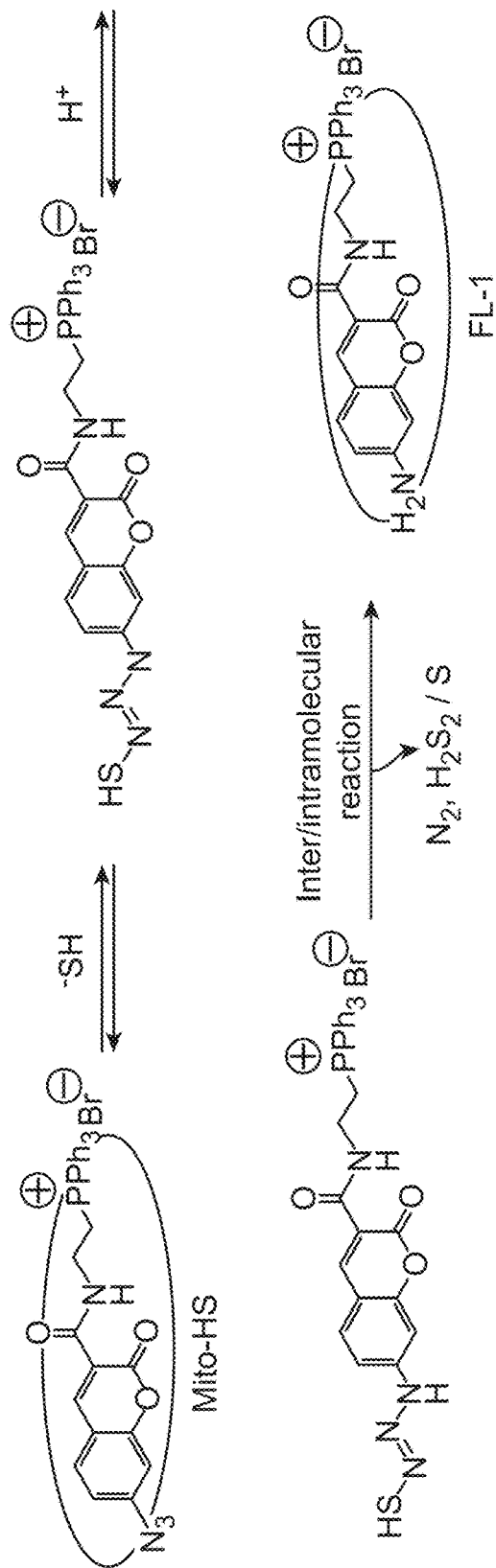
FIG. 2B shows a reaction scheme for detecting endogenous hydrogen sulfide using Mito-HS.

In some embodiments, a method 200 for detecting hydrogen sulfide in a sample is provided as illustrated in FIG. 2A. In step 202, samples containing a population of cells are obtained from one or more subjects. In some embodiments the sample is pretreated with one or more agents. The agent may be a thiol-masking reagent including N-ethyl maleimide (NEM). The population of cells may include one or more cell types including cancer cells, cells from adipose, muscle, cartilage, bone, mucosa, lung, heart cells, brain, liver, kidney, pancreas, or vasculature, or a combination thereof. In step 204, the sample is contacted with a composition including a suitable amount of the compound I for a predetermined time period. The sample may be contacted with the composition including 0.01 to 1000 μM of Mito-HS. The time period may be in the range of 1 min to 1 h. In step 206, a change in fluorescence is detected by exciting a laser source at excitation in the range of 300-600 nm and monitoring fluorescence at emission in the range of 300-600 nm. In step 208, the $H_2S$ level in the sample is detected. The detection may be done by visualizing the fluorescence using microscopy. A comparison of the relative levels may be made against a standard or control sample to determine relative $H_2S$ levels. The change in fluorescence may be indicative of disease relapse or outcome in a subject. In other embodiments, a method of detecting hydrogen sulfide is as depicted in FIG. 2B.

Although the detailed description contains many specifics, these should not be construed as limiting the scope of the invention but merely as illustrating different examples and aspects of the invention. It should be appreciated that the scope of the invention includes other embodiments not discussed herein. Various other modifications, changes and variations which will be apparent to those skilled in the art may be made in the arrangement, operation and details of the compositions, systems and method of the present invention disclosed herein without departing from the spirit and scope of the invention as described here. While the invention has been disclosed with reference to certain embodiments, it will be understood by those skilled in the art that various changes may be made and equivalents may be substituted without departing from the scope of the invention. In addition, many modifications may be made to adapt to a particular situation or material the teachings of the invention without departing from its scope.

EXAMPLES

Example 1—Synthesis of Mito-HS

A solution of 4-bromo-2-hydroxybenzaldehyde (1.0 g, 4.97 mmol) was prepared by adding in 20 mL of ethanol. Diethylmalonate (955 mg, 5.97 mmol) and piperidine (1.27 g, 14.92 mmol) were added to it followed by continuous stirring for 3 hours at room temperature. Ethanol was evaporated after competition of the reaction. The residue obtained was dissolved in 2N HCl and extracted with ethyl acetate The extracted organic layer was washed with water and brine solution followed by drying over anhydrous sodium sulfate. The organic layer was kept in reduced pressure to get concentrated to obtain white colour solid product (1.20 g, 81.63%), named as compound A.

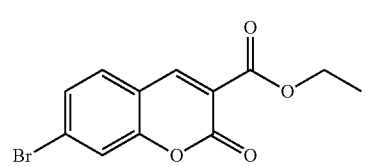

(A)

The yield for the above synthesis was 98.10%, determined by liquid chromatography-mass spectrometry (LCMS). $^1H$ and $^{13}C$ NMR were performed for compound A. $^1$H-NMR (400 MHz, DMSO-d6): δ 8.76 (s, 1H); 7.86 (d, 1H, j=9.08 Hz); 7.78 (s, 1H); 7.62-7.60 (dd, 1H, j=6.88 Hz); 4.30 (q, 2H); 1.30 (q, 3H); $^{13}$C-NMR (100 MHz, DMSO-d6): 162.34, 157.05, 155.32, 154.74, 153.69, 148.09, 147.92, 140.81, 131.55, 130.24, 129.64, 127.95, 127.62, 125.39, 125.19, 119.11, 117.4, 61.25, 47.30, 46.52, 44.09, 25.82, 24.81, 23.82, 22.74, 14.11, 13.85. From the Electrospray ionization-High resolution mass spectrometry (ESI-HRMS) study for compound A, experimental mass (336.02) was found to be approximately equal to calculated mass (336.200).

A solution of compound A (1.3 g, 4.37 mmol) was prepared in 20 mL of DMSO. Sodium azide (341 mg, 5.25 mmol) was added to it followed by continuous stirring for 6 hours at 30° C. After completion of the reaction, ice-cold water was added and stirred for 20 minutes to get a solid precipitation. The solid precipitate was filtered, washed with water and dried in vacuum to obtain a mass of pale brown solid (0.860 g, 75.64%), named as compound B.

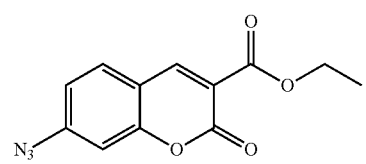

(B)

$^1$H and $^{13}$C NMR were performed for compound B. $^1$H-NMR (400 MHz, DMSO-d6): δ 8.73 (s, 1H); 7.89 (s, 1H); 7.17 (m, 1H); 4.28 (m, 2H); 1.26 (t, 3H, j=6.18 Hz). $^{13}$C-NMR (100 MHz, DMSO-d6): 162.34, 154.73, 147.92, 145.93, 131.55, 127.92, 119.11, 116.49, 115.75, 114.81, 106.32, 61.25, 13.85. From the ESI-HRMS study, experimental mass was found to be 282.060, which is approximately equal to the calculated mass 282.04.

A solution compound B (600 mg, 2.30 mmol) was prepared in NaOH solution (10 mL, 10%) and stirred for 1 h. pH was adjusted to ~3 after completion of the stirring. The solution was extracted with ethyl acetate to obtain organic layers. The layers were washed with water and brine solutions followed by drying over anhydrous sodium acetate and evaporated under reduced pressure to obtain a solid yellow mass (370 mg, 69.16%), named as compound C.

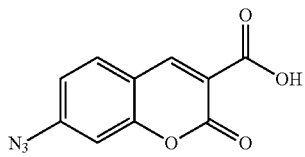

(C)

$^1$H and $^{13}$C NMR were performed for compound C. $^1$H-NMR (400 MHz, DMSO-d6): δ 13.11 (s, 1H), 8.71 (s, 1H), 7.90 (t, 1H, j=6.21 Hz), 7.16 (m, 2H). $^{13}$C-NMR (100 MHz, DMSO-d6): 163.84, 156.39, 155.65, 148.01, 145.74, 131.72, 127.89, 116.25, 115.02, 106.35. From the ESI-HRMS study experimental mass (275.99) was found to be approximately equal to the calculated mass (276.00).

A solution of compound C (340 mg, 1.46 mmol) was prepared in THF (60 mL) at 0° C. Compound D was prepared as described earlier in Maryanoff et al. (Stereochemistry of the Wittig Reaction. Effect of Nucleophilic Groups in the Phosphoniumylide, J. Am. Chem. Soc. 1985, 107, 217-226).

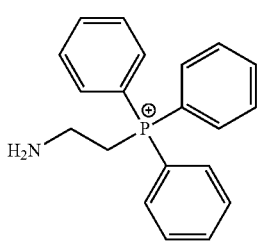

(D)

D (821 mg, 1.78 mmol), HATU (835.0 mg, 2.2 mmol) and DIPEA (1.13 g, 8.8 mmol) were added to the solution and stirred the solution mixture continuously for 12 h at room temperature. The reaction mixture was diluted with water and extracted with ethyl acetate after the completion of the reaction. The extracted organic layer was washed with brine, dried over anhydrous sodium sulfate and evaporated in vacuum to obtain crude product, which was purified by column chromatography over silica gel (100-200 mesh) using methanol in DCM (0.5:9.5) as eluent to obtain a yellow solid mass (295 mg, 38.63%) of Mito-HS, named as I. 98.33% purity for I was observed form the HPLC result $^1$H-NMR (400 MHz, DMSO-d6): δ 8.95 (t, 1H, j=5.89 Hz), 8.78 (s, 1H), 7.98 (s, 1H), 7.86 (m, 9H), 7.75 (m, 6H), 7.29 (m, 1H), 7.22 (dd, 1H, j1=4.89 Hz, j=12.01 Hz), 3.87 (m, 2H), 3.73 (m, 2H), 1.23 (s, 1H). $^{13}$C-NMR (100 MHz, DMSO-d6): 162.47, 155.65, 148.43, 145.92 131.95, 127.92, 119.11, 116.18, 115.89, 114.81, 106.32, 61.08, 13.99. From the ESI-HRMS experimental mass (419.152) was found to be exactly matched the calculated mass of Mito-HS fragment after removal of $N_2$ and the molecular mass peak was at 519.158, approximately matching the calculated result 519.159.

Example 2—Detection of Endogenous H2S Selectively in Cancer Cells

Human cervical cancer cells (HeLa), breast cancer cells (MDA-MB-231), prostate cancer cells (DU 145) and 3T3-L1 fibroblast cells were cultured in DMEM high glucose media supplemented with 10% fetal bovine serum, 1% Penstrep, 0.2% Amphotericin B. The cells were grown overnight at 37° C. incubator with 5% $CO_2$. HeLa, MDA-MB-231, DU 145, and 3T3-L1 cells were seeded at a density of 0.3×10$^6$ cells in 35 mm dish and kept overnight. The probe Mito-HS prepared in Example 1 was dissolved in 0.2% DMSO to make a stock concentration of 10 mM. The cells were treated with 5 μM of Mito-HS for 15 min. 300-550 nm excitation light was used to measure its fluorescence properties. Images were acquired using Zeiss Fluorescence Microscope (A1 Axiovert) with ×40 objective lens.

UV-Vis and fluorescence spectroscopy was studied and changes of Mito-HS was recorded in variable concentrations of $Na_2S$ (0-200 μM) in PBS buffer solution containing 0.2% of DMSO at physiological pH (pH 7.4) to study the performance of the probe in $H_2S$ ($Na_2S$) environment as shown in FIG. 3A-C. In FIG. 3A, the UV-Vis absorption band at $λ_{ab}$ 370 nm gradually decreases with the appearance of a new absorption band at $λ_{ab}$ 395 nm in the presence of variable concentrations of $H_2S$. Also, in FIG. 3B, a gradual increase in fluorescence intensity at $λ_{max}$ 450 nm upon addition of H2S (0-200 μM) to the Mito-HS was observed followed by saturation point was reached at 200 μM of $H_2S$. The fluorescence intensity of Mito-HS was observed to be ~43 fold higher in the presence of $H_2S$ (200 μM). From the results, it was determined that Mito-HS is capable of detecting $H_2S$ in physiological (10-600 μM) condition, however lower detection limit was calculated by applying regression equation; which was found to be 24.3 nM.

Figure 4A:
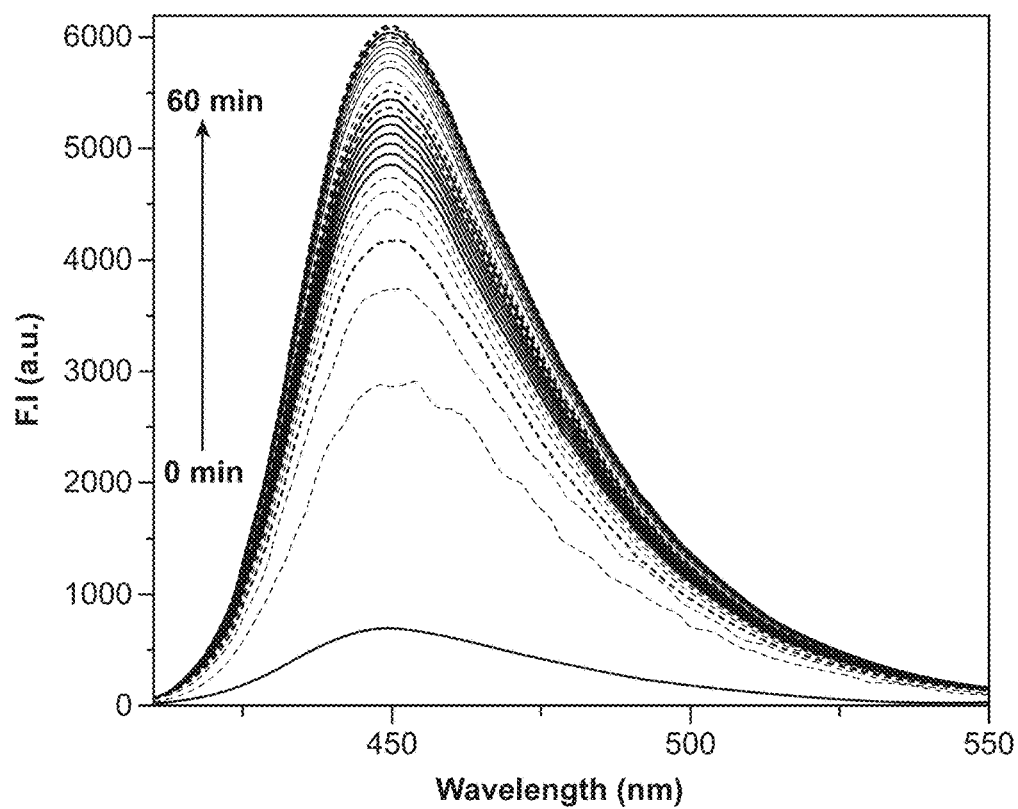
FIG. 4A shows fluorescence change of Mito-HS (5 mM) with $Na_2S$ (100 mM) in PBS buffer solution (pH=7.4; 0.2% DMSO) at 37° C.
Figure 4B:
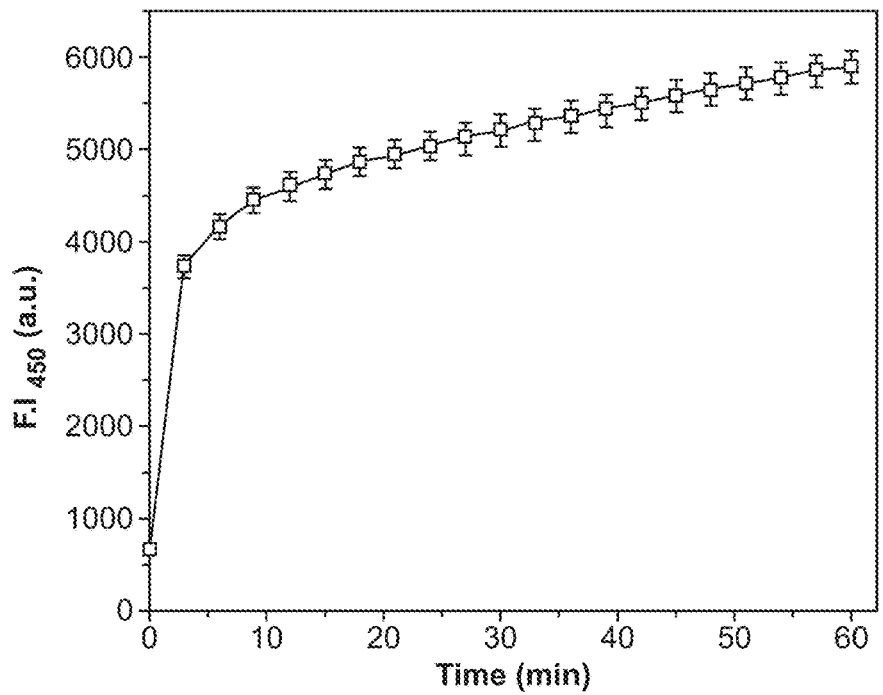
FIG. 4B shows fluorescence change of Mito-HS (5 mM) with Na$_2$S (100 mM) at different time intervals in PBS buffer solution (pH=7.4; 0.2% DMSO) at 37° C.

The environment of biological entities in cellular milieu is temporal, henceforth, the response time of probe for an analyte is crucial. Thus, time-dependent fluorescence data at λmax 450 nm were recorded in the presence of $H_2S$ (20.0 eq.). FIG. 4 indicates that the fluorescence intensity gradually increased with time and plateaued beyond 40 min. The rate of reaction of Mito-HS with $H_2S$ was calculated to be $5.4×10^{-3}$ $s^{-1}$. This demonstrates the ability of Mito-HS to provide real-time information on $H_2S$ formation in the cellular microenvironment.

Example 3: Selectivity Study of Mito-HS in Cellular Milieu

Figure 5:
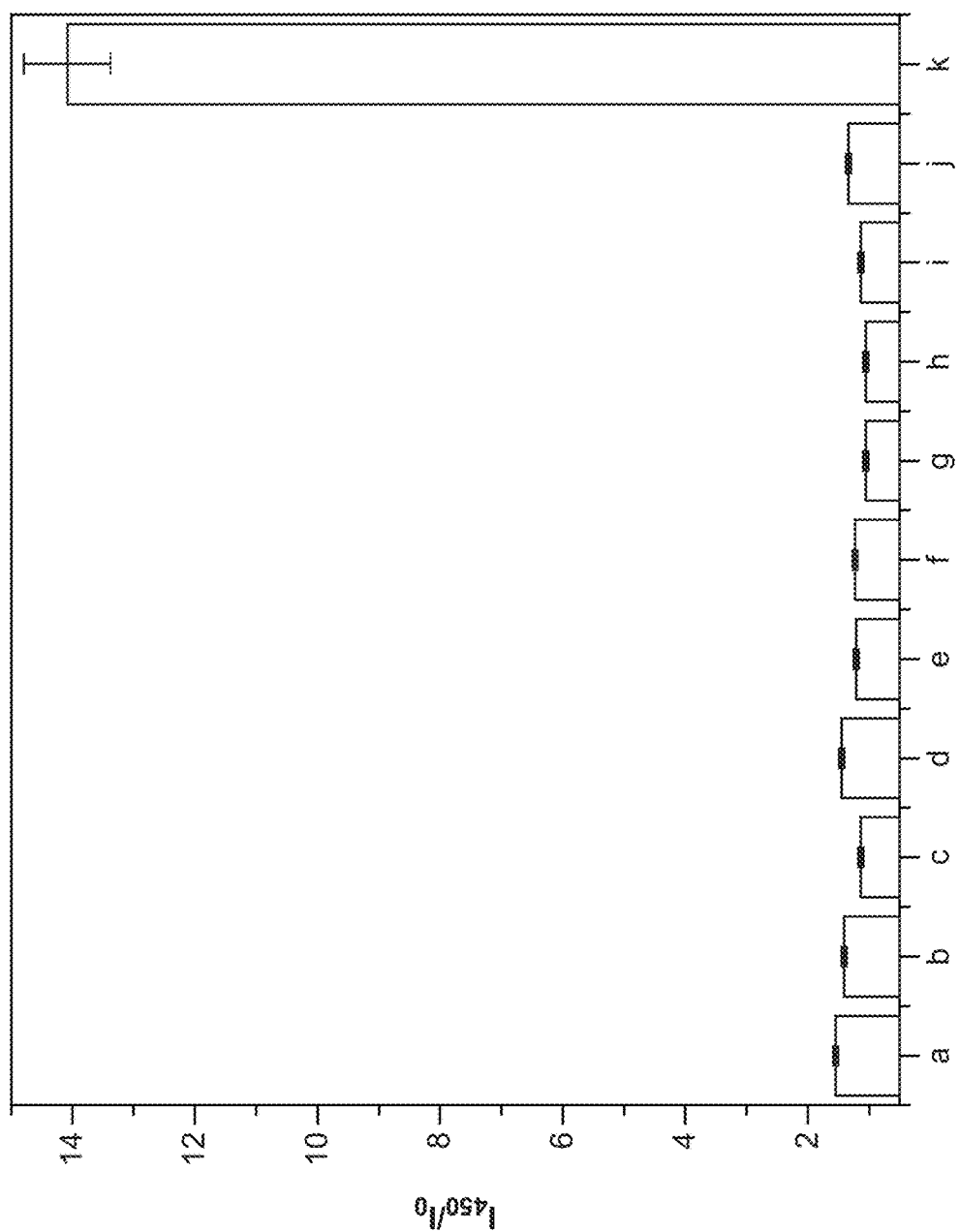
FIG. 5 shows fluorescence responses of the probe (5 µM) in the presence of various biological important analytes (a) cysteine (Cys), (b) H$_2$O$_2$, (c) NaNO$_2$. (d) Cu(OAc)$_2$, (e) Zn(OAc)$_2$, (f) FeSO$_4$, (g) FeCl$_3$, (h) Na$_2$CO$_3$, (i) GSH, (j) ascorbic acid (AA) and (k) Na$_2$S in aqueous solutions (in PBS, 0.2% DMSO, pH=7.4) at 37° C.

Fluorescence responses of Mito-HS (5 μM) in the presence of various biologically important analytes such as $H_2S$, cysteine (Cys), $H_2O_2$, $NaNO_2$, $Cu(OAc)_2$, $Zn(OAc)_2$, $FeSO_4$, $FeCl_3$, $Na2CO_3$, GSH, and ascorbic acid (AA) NO, $Na_2S_2O_4$ in aqueous solutions (in PBS, 0.2% DMSO, pH=7.4) at 37° C. were studied as shown in FIG. 5. Excitation wavelength was set at 380 nm and excitation and emission slit widths both set at 3 nm. Error bars were obtained from triplet experimental data. It was observed that none of the analytes showed considerable fluorescence change other than $H_2S$. So, the experiment supported the proposed concept of using Mito-HS to track cellular $H_2S$ over other competing substances such as thiols.

Example 4: Physiological pH Stability Studies of Mito-HS

Figure 6B:
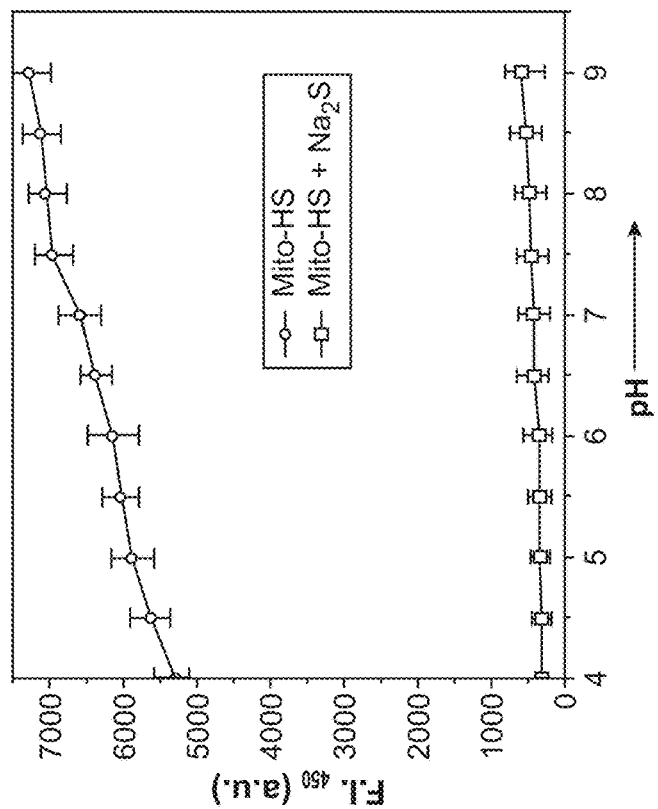
FIG. 6B shows fluorescence intensity of Mito-HS (5 µM) in presence of Na$_2$S (100 µM) and in absence of Na$_2$S at various pH (pH 4-9) in PBS buffer solution (pH=7.4; 0.2% DMSO) at 37° C.
Figure 6A:
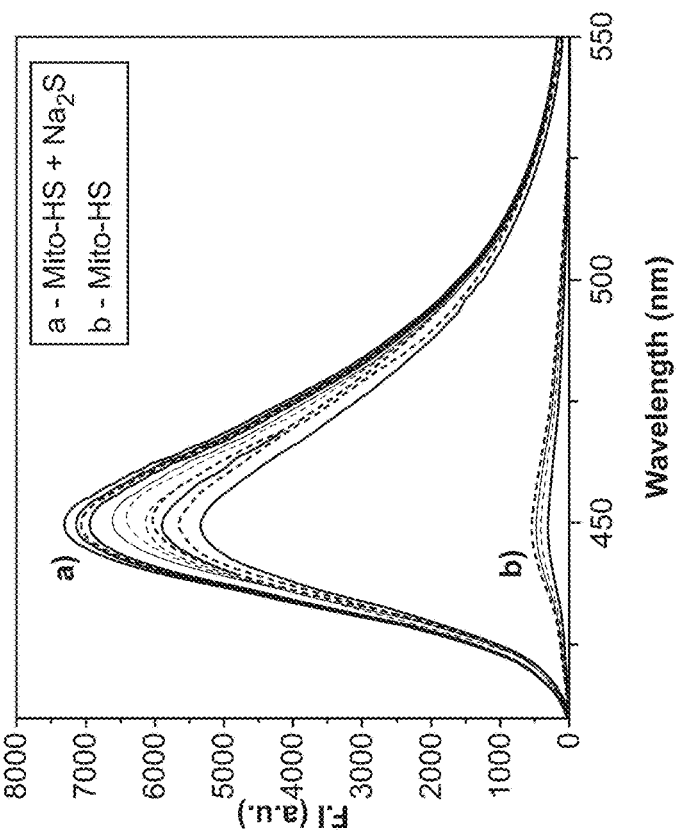
FIG. 6A shows fluorescence intensity of Mito-HS (5 µM) (a) in presence of Na$_2$S (100 µM) and (b) in absence of Na$_2$S.

The stability and reactivity of Mito-HS toward H2S in various physiological pH was studied in fluorescence spectrometry as shown in FIG. 6. The result indicates that Mito-HS was found to be stable in the pH range 4-9, whereas high fluorescence intensity was observed in $H_2S$ environment with sharp depreciation in lower pH range. This suggests that Mito-HS is appropriate to be used in cellular milieu to detect H$_2$S.

Example 5: Estimation of Ability of Mito-HS to Detect H2S in Blood Serum

Figure 7A:
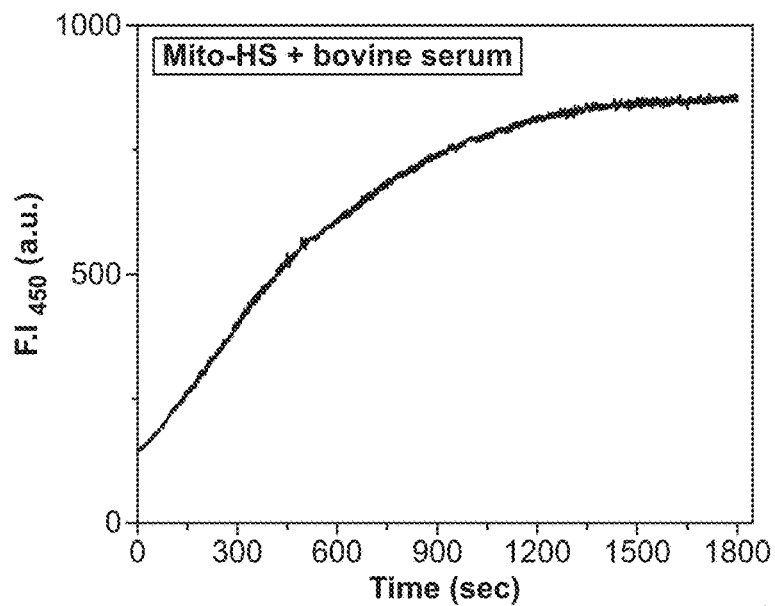
FIG. 7A illustrates the ability of Mito-HS to detect hydrogen sulfide in blood samples with selectivity.

Fluorescence spectroscopy was performed for Mito-HS in fetal bovine serum at 37° C. Excitation and emission wavelengths were set at 380 nm and 450 nm respectively and slit widths at 3 nm. The result obtained from FIG. 7A indicates that Mito-HS had 30-fold increased intensity in blood serum (0.45 mM albumin protein).

Example 6: In Vitro Cytotoxicity Study

Figure 7B:
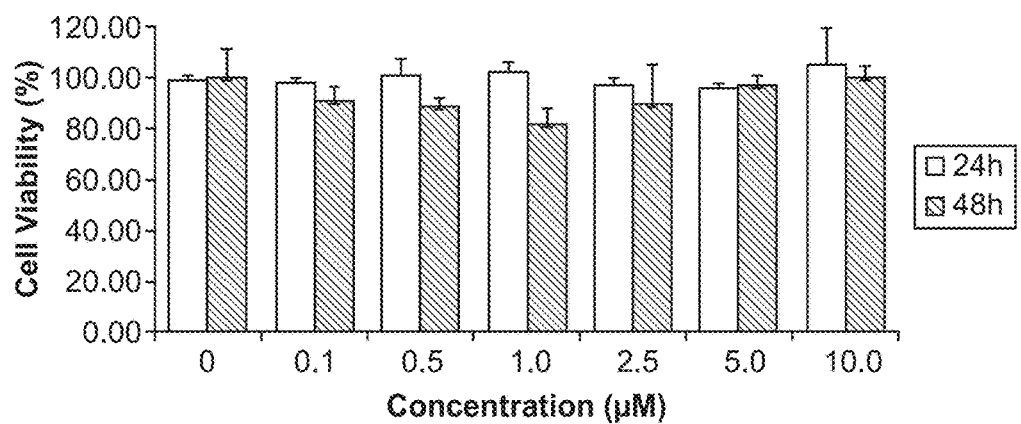
FIG. 7B shows cell viability of HeLa cells treated with various concentrations (0, 0.1, 0.5, 1, 2.5, 5 and 10 µM) of Mito-HS. The cells were incubated for 24 and 48 h after treatment of Mito-HS.
Figure 7C:
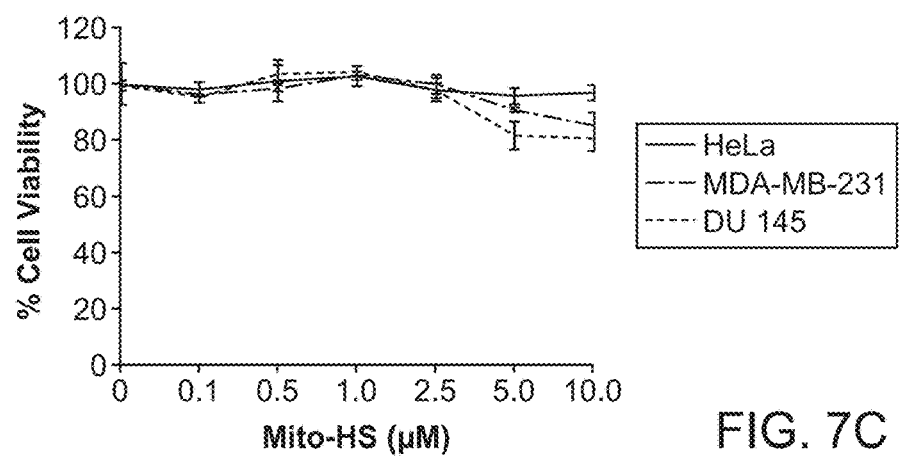
FIG. 7C shows cell viability of HeLa, MDA MB 231 and DU 145 cells.
Figure 8A:
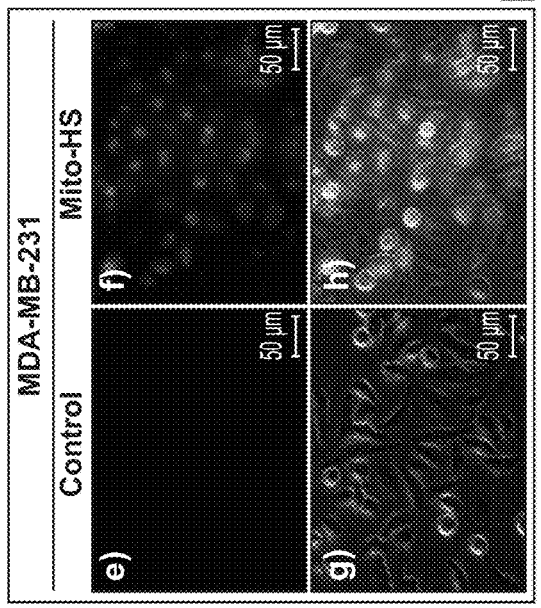
FIG. 8A shows fluorescent microscopic images of untreated HeLa cells (a), those treated with Mito-HS (5 µM) (b) along with their corresponding overlay of the fluorescence images with DIC bright field images (c and d).
Figure 8B:
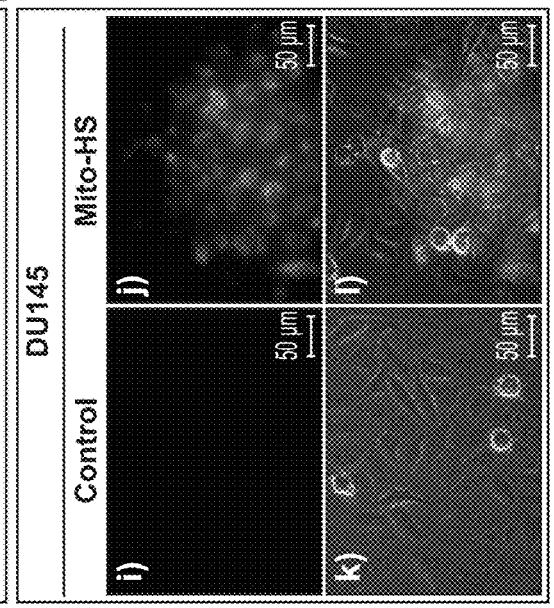
FIG. 8B shows fluorescent microscopic images of untreated MDA-MB-231(e), those treated with Mito-HS (5 µM) (f) along with their corresponding overlay of the fluorescence images with DIC bright field images (g and h).
Figure 8C:
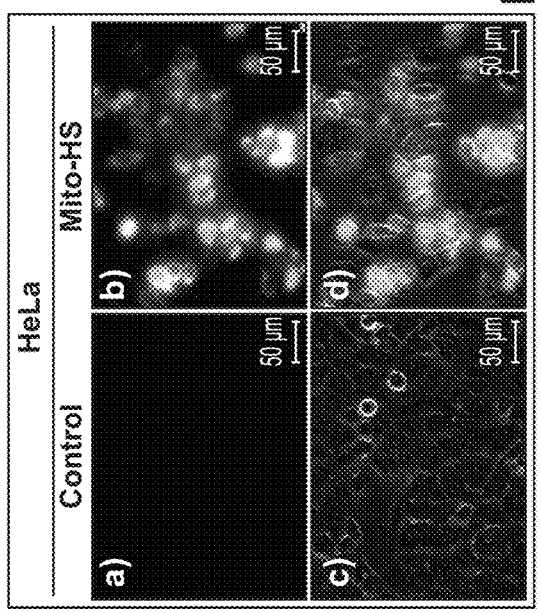
FIG. 8C shows fluorescent microscopic images of untreated 3T3-L1 (m) cells and those treated with Mito-HS (5 µM) (n) along with their corresponding overlay of the fluorescence images with DIC bright field images (o and p).
Figure 8D:
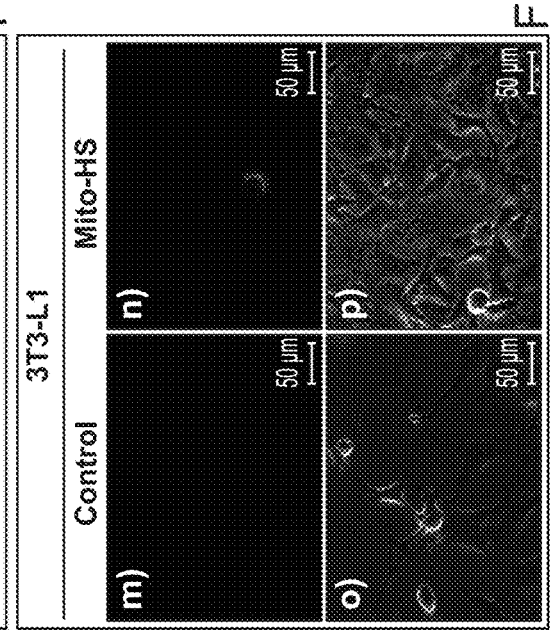
FIG. 8D shows fluorescent microscopic images of untreated DU145 (i) cells and those treated with Mito-HS (5 µM) (j) along with their corresponding overlay of the fluorescence images with DIC bright field images (k and l).

Prior to the application of probe in vitro, cytotoxicity study was performed to check its biocompatibility. HeLa, MDA-MB-231 and DU145 cells were considered to assess the cytotoxicity of Mito-HS by conventional MTT assay. The cells were treated with Mito-HS and incubated for 48 h. The cell viability vs. concentration bar graph as shown in FIGS. 7B and C indicate that Mito-HS did not show cytotoxic behavior against the three cancer cells.

Example 7: Determination of Fluorescence Quantum Yield

The fluorescence quantum yield of Mito-HS was determined in the presence and absence of H$_2$S in PBS buffer solution of 10 mM concentration and in the physiological pH of 7.4 taking quinine ($\Phi_X$=0.542) as standard. The fluorescence quantum yield was calculated by the equation: $\Phi_S = \Phi_X (A_S F_S / A_X F_X)$, where, $A_S$ and $A_X$ are the absorbance of the sample and the reference, respectively; at the same excitation wavelength, $F_S$ and $F_X$ are the corresponding relative integrated fluorescence intensities. The quantum yield for Mito-HS calculated to be 0.045 was increased to 0.479 due to formation of FL-1 in the presence of H$_2$S.

Example 9: Fluorescence Microscopic Study of Mito-HS in Cancer and Normal Cells Fluorescence microscopic study was performed for Mito-HS treated and untreated cancer cells (HeLa, MDA-MB-231 and DU145 cells) and normal cell (3T3-L1 cells) by illuminating lights of 390 nm as excitation wavelength and monitoring the emission over 440-500 nm range. The results in FIG. 8A-D indicates that Mito-HS (5.0 μM) pretreated cancer cells were shown strong fluorescence images (b, f, j). The merged fluorescence images with their corresponding bright-light images as shown in FIG. 8A-D (d, h, l). In contrast, Mito-HS pretreated normal cells were remained non-fluorescent under similar conditions even after an hour. The insufficient production of H$_2$S in 3T3-L1 cells was responsible for their non-fluorescent images. The comparative study suggests that Mito-HS is capable of distinguishing cancer cells from normal cells by labeling the cells depending upon the extent of H$_2$S formation in 15 minutes.

To assure that the fluorescence image of the Mito-HS treated cells were solely due to production of endogenous H2S instead of any other endogenous thiol-like entities such as GSH, cysteine and homocysteine, HeLa, MDA-MB-231 and DU145 cells were pretreated with a thiol-masking agent, here N-ethyl maleimide (NEM). The NEM treated cells were observed to be equally fluorescent labeled like the NEM untreated HeLa cells in FIG. 9A-C. These results suggest that Mito-HS can selectively detect endogenous H2S production in HeLa, MDA-MB-231 and DU145 cells without affected by thiol containing entities in the cellular milieu.

Cystathionine-β-synthase (CBS) and cystathionine-γ-lyase (CSE) are reported to produce endogenous H2S in the cancer cells. To justify this, HeLa, MDA-MB-231 and DU145 cells were separately pre-treated with aminooxyacetic acid (AOAA) and N-propargylglycine (PAG) respectively. AOAA or PAG or combination of both inhibits the overproduction of CSE and CBS in cancer cells. In FIG. 10A, Mito-HS showed reduced fluorescence in inhibitor treated HeLa cells. The inhibitors suppressed CBE and CSE, which as a result decreased the production of H$_2$S. Quantitative decrease in the fluorescence intensity of AOAA and PAG pretreated HeLa cells, in comparison to untreated cells was calculated by ImageJ software. The decrease in intensity was ~7 to 8 fold in the presence of individual inhibitors or the combination of both as shown in FIG. 10A. Similarly, quantification of fluorescent intensity of inhibitor treated Mito-HS and untreated Mito-HS was studied for MDA-MB-231 and DU145 cells using ImageJ software. AOAA and PAG individually reduced the formation of H$_2$S in both MDA-MB-231 and DU145 cells, which were quantified to be ~2 to 3 fold decrease in inhibitor pretreated cells. The combination of AOAA and PAG substantially decreased H$_2$S production by ~7.5-fold in the cells as shown in FIGS. 10 (B) and 10 (C) respectively. From the experiment, it's suggested that cystathionine-β-synthase (CBS) and cystathionine-γ-lyase (CSE) are over produced in cancer cells e.g. HeLa, MDA-MB-231, and DU145 in comparison to e.g. 3T3-L1 cells.

Example 10: Co-Localization Experiment of Mito-HS with MitoSox Red

Figures 11A, 11B, 11C:
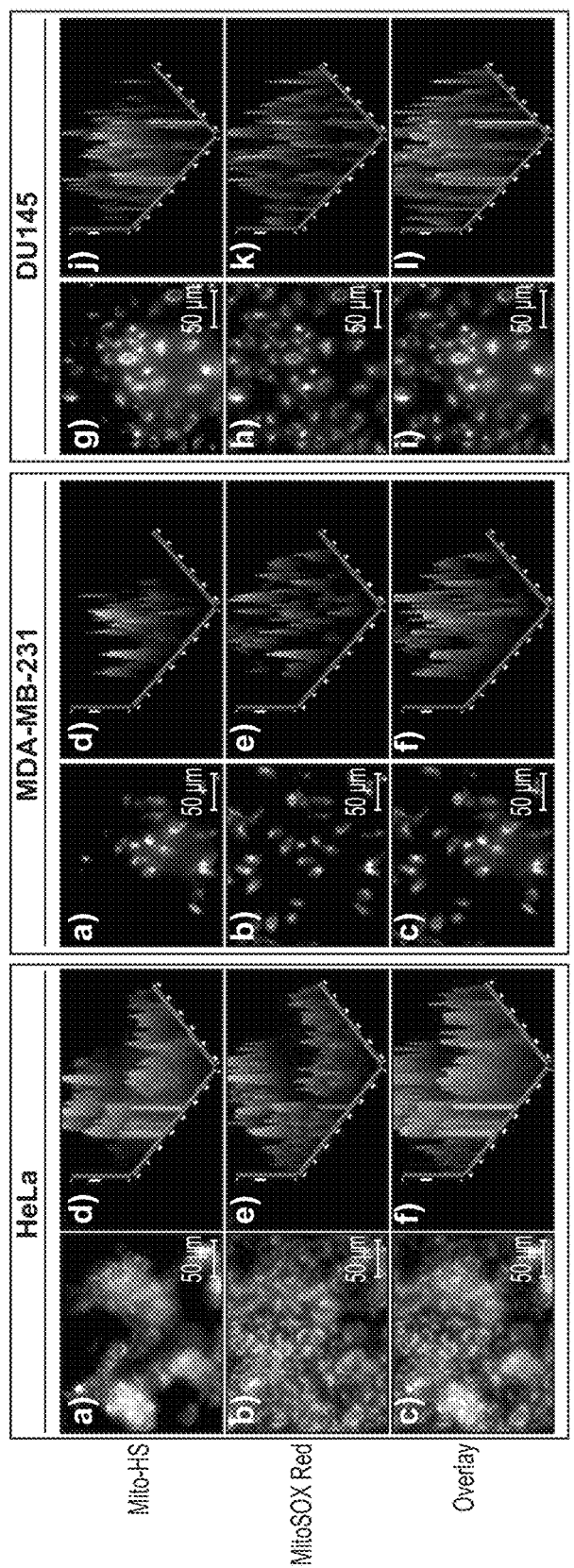
FIG. 11A shows fluorescence and co-localization images of Mito-HS with MitoSOX Red in HeLa cells.
FIG. 11B shows fluorescence and co-localization images of Mito-HS with MitoSOX Red in MDA MB 231 cells.
FIG. 11C shows fluorescence and co-localization images of Mito-HS with MitoSOX Red in DU145 cells.

In order to evaluate the mito-targeting nature of Triphenylphosphonium ion of Mito-HS, a co-localization experiment was carried out with MitoSox Red, which is a mitochondria targeting dye, to make a comparison study. The 3D images of FIG. 11A-C illustrate the localization of Mito-HS predominantly in mitochondria.

What is claimed is:
1. A compound represented by formula I

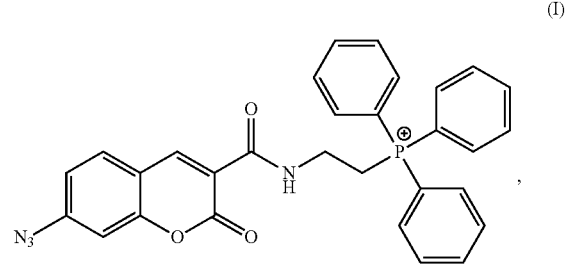 [SMILES: [N-]=[N+]=Nc1ccc2cc(C(=O)NCC[P+](c3ccccc3)(c3ccccc3)c3ccccc3)c(=O)oc2c1]

or a pharmaceutically acceptable salt thereof.
2. A pharmaceutical composition comprising the compound of claim 1, and a pharmaceutically acceptable carrier.
3. A composition for detecting a disease, guiding disease therapy, predicting disease relapse or prognosticating disease outcome in a subject, the composition comprising a suitable amount of the compound of claim 1.

4. The composition of claim 3, wherein the disease is a neurodegenerative disorder, diabetes mellitus, hypertension, dementia, cirrhosis, gastric mucosal injury, cardiovascular disease, hypoxia, or cancer.

5. The composition of claim 4, wherein said neurodegenerative disorder is Alzheimer's disease or Parkinson's disease.

6. The composition of claim 4, wherein said cancer is cervical cancer, breast cancer, lung cancer, brain cancer, liver cancer, pancreatic cancer, colon cancer, leukemia, bone cancer, blood cancer, or ovarian cancer.

7. The composition of claim 3, further comprising a monoclonal antibody, D-biotin, folic acid, or a combination thereof.

8. The composition of claim 3, wherein the composition is stable over a pH range of 4 to 9.

9. The composition of claim 3, wherein the compound is present in an amount in the range of 1 µM to 100 µM.

10. A composition for detecting hydrogen sulfide in a sample comprising a population of cells, the composition comprising a suitable amount of the compound of claim 1.

11. The composition of claim 10, wherein the population of cells comprise cancer cells, cells from adipose, muscle, cartilage, bone, mucosa, lung, heart cells, brain, liver, kidney, pancreas, or vasculature, or a combination thereof.

12. The composition of claim 10, wherein the composition is at least 100 fold to 1000 fold selective for hydrogen sulfide over cysteine (Cys), $H_2O_2$, $NaNO_2$, $Cu(OAc)_2$, $Zn(OAc)_2$, $FeSO_4$, $FeCl_3$, $Na_2CO_3$, GSH, or ascorbic acid (AA).

13. The composition of claim 10, wherein the suitable amount of the compound is in the range of 10 µM to 600 µM.

14. The composition of claim 10, further comprising a monoclonal antibody, D-biotin, folic acid, or a combination thereof.

15. The composition of claim 10, wherein said composition is configured to detect endogenous hydrogen sulfide levels in cells in the absence of external stimulators.

16. A method of detecting hydrogen sulfide in a sample, comprising the steps of:
  a) providing the sample comprising a population of cells;
  b) contacting the sample with a composition comprising a suitable amount of the compound of claim 1 for a predetermined time period; and
  c) detecting a change in fluorescence for the sample using a fluorescence detector;
  wherein the sample is excited in the range of 300 nm to 550 nm and the emission is detected in the range of 300 nm to 550 nm.

17. The method of claim 16, wherein said composition is configured to detect endogenous hydrogen sulfide levels in cells in the absence of external stimulators.

18. The method of claim 16, wherein the suitable amount is in the range of 10 µM to 600 µM.

19. The method of claim 16, further comprising: pretreating the sample with a thiol-masking reagent.

20. The method of claim 19, wherein the thiol-masking reagent is N-ethyl maleimide (NEM).

21. The method of claim 19, further comprising visualizing the change in fluorescence using microscopy.

22. The method of claim 19, wherein the population of cells comprise cancer cells, cells from adipose, muscle, cartilage, bone, mucosa, lung, heart cells, brain, liver, kidney, pancreas, or vasculature, or a combination thereof.

23. The method of claim 16, further comprising determining the change in fluorescence of the sample is greater than that of a standard sample.

24. The method of claim 23, wherein the change in fluorescence is indicative of disease relapse or outcome.

25. The method of claim 16, wherein the composition further comprises one or more agents selected from monoclonal antibody, D-biotin, folic acid, or a combination thereof.

26. A process for preparing the compound of claim 1, the process comprising the steps of:
  a) adding 4-bromo-2-hydroxybenzaldehyde to a first solution comprising dimethylmalonate and piperidine to form a first compound represented by formula A;

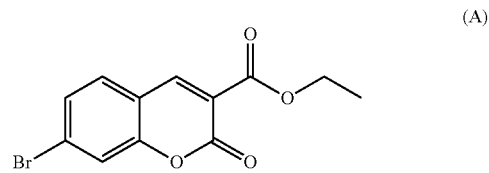 [SMILES: CCOC(=O)c1cc2ccc(Br)cc2oc1=O]

(A)

b) adding the first compound (A) in a second solution comprising sodium azide to form a second compound represented by formula B;

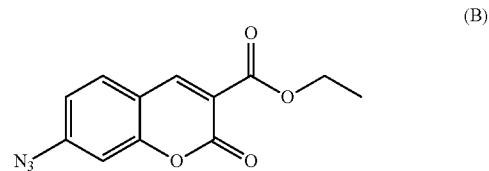 [SMILES: CCOC(=O)c1cc2ccc(N=[N+]=[N-])cc2oc1=O]

(B)

c) adding the second compound (B) to a third solution comprising NaOH to form a third compound represented by formula C; and

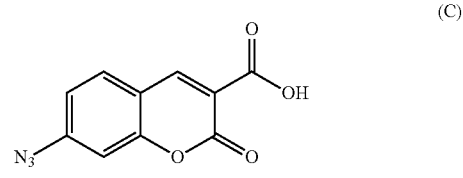 [SMILES: [N-]=[N+]=Nc1ccc2cc(C(=O)O)c(=O)oc2c1]

(C)

d) adding the third compound (C) to a fourth solution comprising a fourth compound represented by formula D,

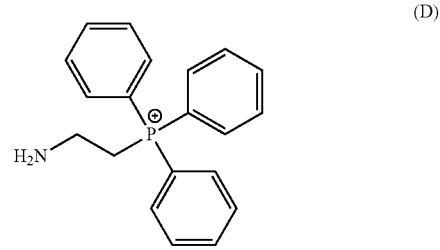 [SMILES: NCC[P+](c1ccccc1)(c1ccccc1)c1ccccc1]

(D)

and a coupling agent to form the compound of claim 1.

* * * * *